United States Patent
Giori et al.

(10) Patent No.: US 8,568,806 B2
(45) Date of Patent: *Oct. 29, 2013

(54) STABLE AND BIOAVAILABLE COMPOSITIONS OF ISOMERS OF LYCOPENE FOR SKIN AND HAIR

(75) Inventors: Andrea Giori, Milan (IT); Federico Franceschi, Milan (IT)

(73) Assignee: Indena, S.p.A., Milan (IT)

( * ) Notice: Subject to any disclaimer, the term of this patent is extended or adjusted under 35 U.S.C. 154(b) by 262 days.

This patent is subject to a terminal disclaimer.

(21) Appl. No.: 12/376,457

(22) PCT Filed: Jul. 30, 2007

(86) PCT No.: PCT/EP2007/006747
§ 371 (c)(1),
(2), (4) Date: Apr. 8, 2010

(87) PCT Pub. No.: WO2008/017401
PCT Pub. Date: Feb. 14, 2008

(65) Prior Publication Data
US 2010/0190867 A1    Jul. 29, 2010

(30) Foreign Application Priority Data
Aug. 8, 2006 (EP) .................... 06016475

(51) Int. Cl.
*A61K 36/00* (2006.01)
(52) U.S. Cl.
USPC ........................................ 424/777; 424/725

(58) Field of Classification Search
None
See application file for complete search history.

(56) References Cited

U.S. PATENT DOCUMENTS

| | | | | |
|---|---|---|---|---|
| 5,837,311 A | * | 11/1998 | Zelkha et al. | 426/651 |
| 5,849,787 A | * | 12/1998 | Fujiwara et al. | 514/458 |
| 5,965,183 A | * | 10/1999 | Hartal et al. | 426/250 |
| 6,797,303 B2 | * | 9/2004 | Zelkha et al. | 426/431 |
| 7,582,325 B2 | * | 9/2009 | Giori | 426/615 |
| 2005/0153038 A1 | * | 7/2005 | Giori | 426/478 |
| 2007/0098820 A1 | * | 5/2007 | Bortlik et al. | 424/725 |
| 2008/0038391 A1 | * | 2/2008 | Giori et al. | 424/776 |

FOREIGN PATENT DOCUMENTS

WO    WO 2005/075575    *    8/2005

OTHER PUBLICATIONS

Shi et al. J. Food Process Engineering. 2003. vol. 25, pp. 485-498.*
Calvo et al. Alimentaria. 2006. vol. 374, pp. 104-105.*
Cookbook entitled "West Bend—Slow Cooking for Fast Meals". Copyright 1991, West Bend Co., West Bend, WI; pp. 5, 18, 20, 26, and 27.*
Lambelet et al., "Improving the stability of lycopene Z-isomers in isomerised tomato extracts", Food Chemistry 112:156-161 (2009).

* cited by examiner

*Primary Examiner* — Chris R Tate
(74) *Attorney, Agent, or Firm* — Porzio, Bromberg & Newman, P.C.

(57) ABSTRACT

The present invention relates to a method of manufacturing a stable composition enriched in cis-lycopene (z-isomers) by prolonged heating in solvents of tomatoes, parts of tomatoes, derivative thereof or tomato extracts in solvents.

4 Claims, 1 Drawing Sheet

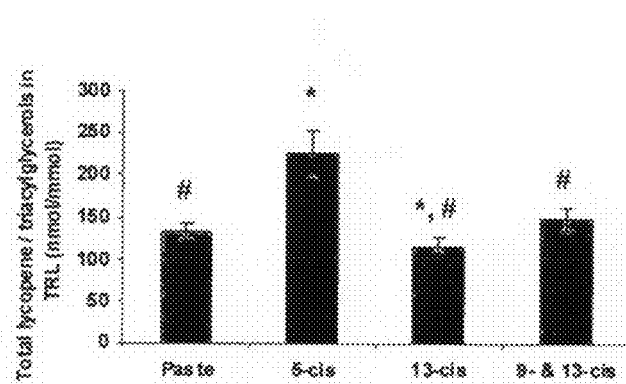
* Significantly different from tomato paste, p < 0.05
Significantly different from 5-Z tomato oleoresin, p < 0.05.

STABLE AND BIOAVAILABLE COMPOSITIONS OF ISOMERS OF LYCOPENE FOR SKIN AND HAIR

CROSS REFERENCE TO RELATED APPLICATION

This is a National Stage of International Application PCT/EP2007/006747, filed 30 Jul. 2007, which claims the benefit of Application No. 06016475.3, filed in Europe on 8 Aug. 2006, the disclosures of which Applications are incorporated by reference herein.

The present invention relates to a primary composition that includes at least one lycopene-containing material enriched in Z-isomers of the lycopene compound having an increased stability and bioavailability, and process of forming the same. It also relates to an oral composition that contains the primary composition in a foodstuff, in a food supplement, in a cosmetic preparation or in a pharmaceutical preparation.

TECHNOLOGICAL BACKGROUND

Absorption of carotenoids is a complex process involving release from the food microstructure matrix, dissolution into mixed micelles, intestinal uptake, incorporation into chylomicrons, distribution to the tissues, uptake by liver and re-secretion into VLDL, which are progressively transformed into LDL.

Lycopene absorption from food sources is widely documented. Lycopene bioavailability is quite low from foods such as tomatoes and tomato juice. Up to now, tomato paste is the best known food source for bioavailable lycopene. Tomato contains about >90% of lycopene in its all E configuration.

Tomato extracts containing a high amount of lycopene are commercially available in the form of oleoresin but the bioavailability of the lycopene in humans is rather limited from these sources. In concentrated tomato extracts, lycopene is mainly present in crystalline form, which has been suggested to be one of the primary factors that reduces its bioavailability.

To date, most commercially available lycopene sources display an isomeric profile quite similar to the starting tomatoes or show only a slight increase in Z-isomers, whether they are derivatives (such as sauces) or extracts. A number of treatments, as for instance thermal processing, are known to promote isomerization. Shi et al., Journal of Food Process Engineering 2003, 25, 485-498, showed that an increase in Z isomers could be obtained by heating tomato sauces. However certain lycopene isomers are not stable and prone to retro-isomerisation. According to the literature, 5-Z is the most stable among the predominant lycopene isomers followed by the all-E, the 9-Z and the 13-Z. Accordingly, the stability of isomerised lycopene based products depends on their lycopene isomer profile and thus can be modulated by technological processings affecting this profile.

Thermal isomerisation of lycopene is known to improve its bioavailability from food matrices. However, the bioavailability of individual lycopene isomers has not been investigated yet. As for stability, it can be assumed that bioavailability of lycopene based products is dependent on their lycopene isomer profile and thereby can be modulated by technological means.

There are already patents that propose technological means and formulations for improved bioavailibility of lycopene.

For example, WO 2005/075575 provides a primary composition enriched in Z-isomers, effective to increase the bioavailability of lycopene.

EP 1 103 579 discloses a process for extracting lycopene by refluxing ethanol: the process is carried out for short time (30') so that no significant isomerization occurs. Actually, the natural all-Z lycopene is desired as the final product.

WO 96/13178 discloses a process for the preparation of stable lycopene concentrates: the effect of isomerization on stability is not however appreciated and, on the contrary, the disclosed process tries to avoid isomerization by using temperatures lower than 50° C. for a few minutes, e.g. 10 minutes.

EP 1 201 762 refers to a lycopene-containing product wherein lycopene is in its natural all-trans form. No significant isomerisation takes place since any heat treatment (dissolution and concentration) is carried out for the shortest possible time (less than 1 hour).

KR 2005 006592 discloses the preparation of a lycopene-zinc complex having increased anti-oxidant activity. Hating is applied in the absence of solvents to break the cell walls of the plant material. No prolonged heating and no isomerization occurs.

WO 03/079816 discloses a process for the preparation of tomato extracts with high content in lycopene wherein the extraction is carried out at room temperature.

U.S. Pat. No. 5,837,311 and WO 97/48287 disclose a process for the preparation of an oleoresin having high content of lycopene and satisfactory stability. The latter feature is obtained by means of phospholipids and glycerides present in the oleoresin itself. No mention is made about the isomeric composition of lycopene and of its influence on the stability. An hot extraction is carried out in order to maximise the yield in lycopene but for times not longer than 1.2 hours. A heat pre-treatment is carried out on the tomatoes in the absence of any solvent only in order to improve the pulp-serum separation.

WO 2005/075575 addresses the problem of increasing the cis-isomers content in tomato oleoresins: isomerization is obtained, inter alia, by thermal treatment for short period of time. Moreover, the obtained product contains an high amount of the unstable 13-cis isomer.

EP 0 937 412 discloses a process for the preparation of finely divided pulverous carotenoid preparations including an heating step in the presence of solvents for very short times (5 seconds).

U.S. Pat. No. 5,858,700 concerns a process for the isolation and purification of lycopene crystals characterised by the hydrolysis of impurities such as glycerides and phosphonates. The hydrolysis is carried out at high temperature but for times shorter than 2 hours, optionally preceded by an extraction step with refluxing solvents, but always for short time in order to prevent the lycopene degradation.

U.S. Pat. No. 6,235,315 discloses stable, pulverulent lycopene formulations characterised in that lycopene has a certain degree of crystallinity and the lowest possible degree of isomerization.

WO 03/090554 discloses concentrated tomato derivatives having high content of lycopene and pre-determined viscosity and sugar content. The process is physical and no solvent is used. Heating for 1-6 minutes II is carried out on round tomatoes in order to make the pulp separation easier.

Mayer-Miebach at al., "Thermal processing of carrots: lycopene stability and isomerisation with regard to antioxidant potential" Food Research International, Elsevier Applied Science, Barking, GB, vol. 38, no. 8-9, October 2005, pages 1103-1108, study the isomerisation of lycopene in freeze-dried carrots in function of temperature. The Authors conclude that only the all-trans isomer is stable to prolonged heating, resulting in a decrease of cis-isomers.

As a matter of fact, therefore, the prior art does not provide isomerisation processes of lycopene comprising a prolonged heating in organic solvents allowing to obtain a product having high bioavailability and stable isomeric composition.

SUMMARY

It has been found that the stability of individual Z-lycopene isomers varies from one isomer to another; in particular the 13-Z lycopene was much less stable than either the 5-Z, or the 9-Z, or the all-E isomers. Consequently, a primary composition according to the present invention must have a level of 13-Z isomer as low as possible to exhibit optimal stability. It has also been shown that some Z isomers (such as 5-Z and 9-Z, for example) of lycopene enhance the bioavailability of the composition containing lycopene. The primary composition must therefore contain mainly the 5-Z isomer, or a combination of 9-Z and 5-Z isomers to provide an improved bioavailability and bioefficacy.

Accordingly, it is a first object of the present invention to provide primary compositions with at least one lycopene-containing material enriched in a specific mixture of Z isomers of lycopene, the lycopene-containing material containing by weight a greater percentage of an isomer selected from the group consisting of 5-Z, 9-Z and combinations thereof than of 13-Z isomer.

In an embodiment, the present invention provides an oral composition that contains the primary composition in a foodstuff, in a food supplement, in a cosmetic preparation or in a pharmaceutical preparation.

In an embodiment, the present invention provides the primary composition as an additive in a foodstuff for oral administration, such as in a nutritional composition, a food supplement, a pet food product, a cosmetic preparation or a pharmaceutical preparation.

In an embodiment, the present invention provides a method of manufacturing the primary compositions or food supplements, cosmetic preparations or pharmaceutical preparations containing the same.

In another embodiment, the present invention provides the use of the primary composition as described above, for the preparation of an oral, cosmetic or pharmaceutical composition intended for improving skin health, in particular for photoprotection of the skin or for protecting skin tissue against aging.

In an alternative embodiment, the present invention provides the use of the primary compositions for the preparation of an oral, cosmetic or pharmaceutical composition for preventing or treating cardiovascular diseases or cancers.

An advantage of the present invention is to provide compositions of Z isomers of lycopene that exhibit a higher stability, bioavailability and bioefficacy.

Additional features and advantages are described herein, and will be apparent from, the following Detailed Description and the FIGURE.

BRIEF DESCRIPTION OF THE FIGURE

FIGURE. Area under the curve (AUC) of plasma lycopene/triglycerides of TRL following the consumption of a standard meal containing 25 mg total lycopene from either tomato paste (all-E lycopene) or tomato oleoresin rich in 5-Z lycopene (5-Z oleoresin) or tomato oleoresin rich in 13-Z lycopene (13-Z oleoresin) or tomato oleoresin rich in 9 and 13-Z lycopene (9- & 13-Z oleoresin).

DETAILED DESCRIPTION OF THE INVENTION

The present invention generally relates to compositions that provide health benefits. More specifically, the present invention relates to beneficial nutritional compositions that can be used to improve skin and hair and methods regarding the same.

The present invention now makes available to the consumer an improved composition obtained from natural products. The primary composition provides lycopene in a particularly highly bioavailable and/or bioeffective form.

In a preferred embodiment, the invention provides tomato extracts or derivatives thereof with an isomer ratio different from the naturally occurring one in products to date available. In particular, the invention relates to extracts or derivatives with an E isomer content not higher than 60% on total lycopene content, preferably with an E isomer content not higher than 40% on total lycopene content (by HPLC).

In an embodiment, the present invention provides a primary composition containing a specific combination of Z isomers. Preferably, the ratio of Z/E isomers in the primary compositions of the present invention should be above 1.

Moreover, the combination is preferably rich in 5-Z and 9-Z and poor in 13-Z. In a preferred embodiment, the amount of 5-Z and 9-Z is greater than 30% on total lycopene content, preferably greater than 40%, most preferably greater than 50%. Also, the amount of 13-Z is less than 10% on total lycopene, preferably less than 5%, most preferably less than 3% on total lycopene content. By increasing the specific 5-Z and 9-Z isomers and/or decreasing the 13-Z isomers, for example, a stable form of the primary composition that is more bioavailable and more bioeffective can be obtained. Moreover, the extracts or derivatives of the invention are stable under the usual storage conditions and do not undergo retro-isomerization. Under ordinary protective conditions (absence of light and oxygen), the lycopene total content and E isomer content remains constant. The latter does not increase, even when keeping the extracts at room temperature.

Such a profile (i.e. low amount of 13-Z isomer of the lycopene) may be for example obtained by isomerizing lycopene using catalysis on a solid matrix such as clays, or by prolonged heating.

In an embodiment, the lycopene-containing material can be, for example, in the form of an extract, a concentrate or an oleoresin. In the present specification, the term "oleoresin" should be understood to mean a lipid extract of a lycopene-containing material, which includes possibly other carotenoids, triglycerides, phospholipids, tocopherols, tocotrienols, phytosterols and other less significant compounds. It has been surprisingly found that retro-isomerization of lycopene in isomerized tomato oleoresin can be minimized by reducing its content in 13-Z isomer.

In an embodiment, the lycopene-containing material can be an extract, a concentrate or an oleoresin, which is obtained, extracted, enriched or purified from a plant or vegetable material, a microorganism, a yeast or a product of animal origin. It is further subjected to a treatment to increase its Z isomer content of lycopene, as described below.

If the source of lycopene is from plant origin, it may be vegetables, leaves, flowers, fruits and other parts of the plant. In a preferred embodiment, the source of lycopene is tomatoes (i.e., whole tomato, tomato extract, tomato flesh, tomato puree, tomato skin, with or without the seeds). Suitable plant or vegetable concentrates are obtainable e.g. by drying or freeze-drying the fresh-cut plants or vegetables or the respective roots, fruits or seeds thereof and then optionally grinding or granulating the dried material. Suitable methods of obtaining extracts of the above-mentioned plants or vegetables are known in the art. The plant or vegetable extracts can be obtained, for example, by extracting the fresh-cut or processed plants or vegetables or the respective roots, fruits or seeds thereof with water or with one or more food grade solvents or with a mixture of water and one or more food grade solvents. Preferably, the extracts and concentrates according to the present invention may be lipidic or aqueous. Because carotenoids are liposoluble, extraction with water will remove unwanted constituents that are water-soluble such as, for example, sugars, amino acids, soluble proteins and/or organic acids.

If the lycopene-containing material is obtained from microorganism, any microorganism that produces lycopene may be used, in particular probiotic microorganism such as, for example, lactic acid bacterium. Also, the product of animal origin may be from, for example, salmon, shrimps, krill or a liver extract or a milk fraction. In the present specification, the term "milk fraction" should be understood to mean any part of the milk.

In an alternative embodiment, the lycopene-containing material can be an oleoresin. Suitable methods for obtaining oleoresins from the above-mentioned plants or vegetables are well known in the art. For example, oleoresins can be obtained by lipidic extraction using a solvent compatible with the food business, cosmetics or pharmaceuticals. Oleoresins prepared by conventional methods have a content in lycopene of about 0.05% to 50% by weight. Their content of all-E isomer of lycopene is usually higher than that of Z-isomers, e.g. the ratio of Z/E isomers of lycopene in a selected tomato oleoresin is about 7:93.

Oleoresins are preferred starting material for obtaining the primary composition according to the present invention because they contain other carotenoids or antioxidants such as Vitamin E, which also stabilize the composition. The bioactivity and stability of the lycopene compound in the oleoresin can be improved, in particular, during the isomerization process and the yield of the Z lycopene in the primary composition can also be increased.

The lycopene-containing material preferably includes carotenes and xanthophylls such as, for example, zeaxanthine, astaxanthine, beta-cryptoxanthin, capsanthine, canthaxanthine, lutein and derivatives thereof such as esters, for example. The lycopene compounds have been subjected to a treatment to increase the Z isomer fraction in the primary composition.

In order to obtain such an isomer profile, the lycopene-containing material which is in the form of an extract, a concentrate or an oleoresin, is subjected to an isomerization by using neutral, acidic or basic solid catalysts (e.g. clays, zeolites, molecular sieves, ion exchangers) to produce mixtures with high Z/E ratio. The use of solid catalysts to enrich the lycopene in Z-isomers is not polluting and harmful to the food since the catalysts can be conveniently removed by simple filtration or centrifugation. Also, combinations of solid catalysts with other common means (e.g. heat, light and radical initiators) can further enhance the geometrical isomerization.

In another embodiment, the extracts or derivatives according to the invention can be prepared starting from tomatoes, parts of tomatoes (such as the skin), derivatives (such as sauces and concentrates) or extracts. Isomerization is carried out by prolonged heating in a solvent. This finding is surprising in view of contrary teachings which may be derived from the prior art discussed in the section "Background of the Invention".

In particular, when tomatoes or derivatives thereof are used as starting materials, they can be treated with a solvent able to extract lycopene. The resulting extract is then heated, the solvent is removed, thus recovering the isomerized extract.

On the other hand, when an extract or derivative is used as starting material, this is taken up in a solvent, the mixture is heated for a suitable time, then the solvent is removed, thus recovering the isomerized extract. Solvents which can be used for the isomerization step are hydrocarbons, chlorinated hydrocarbons, esters, ketones, alcohols; particularly C3-C10 aliphatic hydrocarbons, C1-C3 chlorinated solvents, C3-C6 esters, C3-C8 ketones and C1-C8 alcohols; more particularly hexane, carbon tetrachloride, ethyl acetate, acetone and butanol. Isomerization in solvents is carried out at temperatures ranging from 50 to 150° C., preferably at temperatures ranging from 60 to 130° C. Isomerization time ranges from 4 to 240 h, preferably from 10 to 180 h.

The Z/E isomer ratio in the primary composition may then be increased up to at least 20:80, preferably between 20:80 and 95:5, more preferably from 30:70 to 90:10. In a preferred embodiment, the (5Z+9Z)/E ratio is above 1, and the 13Z is partly removed.

In an embodiment, the present invention provides a primary composition, in the form of a powder, liquid or gel, comprising a lycopene compound which has a better bioavailability and/or bioefficacy than the compound alone. Also, the primary composition may be in the form of a highly water-dispersible composition, if the powder form is chosen. In this instance, the powder is dispersible in water at ambient temperature. The primary composition also provides carotenoids in a particularly highly soluble form in lipids and organic solvents, less prone to crystallization, and having a lower tendency to aggregate.

In another embodiment of the present invention, the primary composition may be used either alone or in association with other active compounds such as vitamin C, vitamin E (tocopherols and tocotrienols), carotenoids (carotenes, lutein, zeaxanthine, beta-cryptoxanthine, etc.) ubiquinones (e.g. CoQ10), catechins (e.g. epigallocatechin gallate), coffee extracts containing polyphenols and/or diterpenes (e.g. kawheol and cafestol), extracts of chicory, Ginkgo biloba extracts, grape or grape seed extracts rich in proanthocyanidins, spice extracts (e.g. rosemary), soy extracts containing isoflavones and related phytoestrogens and other sources of flavonoids with antioxidant activity, fatty acids (e.g. n-3 fatty acids), phytosterols, probiotic fibers, probiotic microorganisms, taurine, resveratrol, aminoacids, selenium and precursors of glutathione, or proteins such as, for example, whey proteins.

The primary composition can additionally comprises one or more of emulsifiers, stabilizers and other additives. Emulsifiers compatible in the food field are, for example, phospholipids, lecithin, polyoxyethylene sorbitan mono- or tristearate, monolaurate, monopalmitate, mono- or trioleate; a mono- or diglyceride. Any type of stabilizer that is known in the food business, in cosmetics or in pharmaceuticals can be added. Also, flavours, colorants and any other suitable additives known in the food business, in cosmetics or in pharmaceuticals can be added. These emulsifiers, stabilizers and additives can be added according to the final uses of the primary compositions.

In an alternative embodiment, the present invention provides an oral composition comprising the primary composition described above in a foodstuff, in a food supplement, in a pet food product, in a cosmetic preparation or in a pharmaceutical preparation.

In a preferred embodiment, a food composition for human consumption can be supplemented by the primary composition. This food composition may be, for example, a nutritional complete formula, a dairy product, a chilled or shelf stable beverage, a mineral water, a liquid drink, a soup, a dietary supplement, a meal replacement, a nutritional bar, a confectionery, a milk or a fermented milk product, a yoghurt, a milk based powder, an enteral nutrition product, an infant formulae, an infant nutritional product, a cereal product or a fermented cereal based product, an ice-cream, a chocolate, coffee, a culinary product such as mayonnaise, tomato puree or salad dressings or a pet food.

For use in food compositions, the primary composition can be added to the above-mentioned foods or drinks so as to have a daily intake between about 0.001 and 50 mg of lycopene contained in the primary composition. A daily intake of about 5 to 20 mg per day is preferably envisaged.

The nutritional supplement for oral administration may be in capsules, gelatin capsules, soft capsules, tablets, sugar-coated tablets, pills, pastes or pastilles, gums, or drinkable solutions or emulsions, syrups or gels, with a dose of about 0.001% to 100% of the primary composition, which can then be taken directly with water or by any other known means. This supplement may also include a sweetener, a stabilizer, an additive, a flavour or a colorant. A supplement for cosmetic purposes can additionally comprise a compound active with respect to the skin. It should be appreciated that the supplements can be made by any methods known by those skilled in the art.

In another embodiment, a pharmaceutical compositions containing the primary compositions can be administered for prophylactic and/or therapeutic treatments, in an amount sufficient to cure or at least partially arrest the symptoms of the disease and its complications. In the present specification, an amount adequate to accomplish this is defined as "a therapeutically effective dose". Amounts effective for this will depend on the severity of the disease and the weight and general state of the patient.

In prophylactic applications, primary compositions according to the invention can be administered to a patient susceptible to or otherwise at risk of a particular disease. Such an amount is defined to be "a prophylactic effective dose". In this use, the precise amounts again depend on the patient's state of health and weight.

In an alternative embodiment, the primary compositions of the invention can be administered with a pharmaceutical acceptable carrier, the nature of the carrier differing with the mode of administration, for example parenteral, intravenous, oral and topical (including ophthalmic) routes. The desired formulation can be made using a variety of excipients including, for example, pharmaceutical grades of mannitol, lactose, starch, magnesium stearate, sodium saccharin cellulose, magnesium carbonate. The pharmaceutical compositions may be a tablet, a capsule, a pill, a solution, a suspension, a syrup, a dried oral supplement, a wet oral supplement.

Preferably, for humans the pharmaceutical compositions according to the present invention can comprise an amount of the primary composition as described above, for a daily administration, so that the lycopene amount ranges from about 0.01 mg to 100 mg. When administered daily to pets, the lycopene amount can range from about 0.01 mg to 100 mg.

It will be appreciated that the skilled person will, based on his own knowledge, select the appropriate components and galenical form to target the active compound to the tissue of interest, e.g. the skin, colon, stomach, kidney or liver, taking into account the route of administration which may be by way of injection, topical application, intranasal administration, administration by implanted or transdermal sustained release systems, and the like.

In another embodiment, the present invention provides a cosmetic composition comprising the primary composition described above. It may be formulated in lotions, shampoos, creams, sun-screens, after-sun creams, anti-aging creams and/or ointments, for example. Preferably, the content of primary composition can be between $10^{-10}$% and 10% by weight of the cosmetic compositions. More preferably, the cosmetic compositions comprise between $10^{-8}$% and 5% by weight of lycopene. The cosmetic compositions that can be used topically can additionally comprise a fat or an oil which can be used in cosmetics such as, for example, those mentioned in the CTFA work, Cosmetic Ingredients Handbook, Washington.

The cosmetic compositions of the present invention can also include any other suitable cosmetically active ingredients. The composition additionally comprises a structuring agent and an emulsifier. Other excipients, colorants, fragrances or opacifiers can also be added to the cosmetic compositions. It will be appreciated that the present cosmetic products will contain a mixture of different ingredients known to the skilled person, ensuring a fast penetration of the objective substance into the skin and preventing degradation thereof during storage.

It should also be understood that the concepts of the present invention may likewise be applied as an adjuvant therapy assisting in presently used medications. Because the primary compounds of the present invention may easily be administered together with food material, special clinical food may be applied containing a high amount of the primary compositions. It should be clear that on reading the present specification together with the appending claims the skilled person will envisage a variety of different alternatives to the alternative embodiments mentioned herein.

The present invention additionally relates to the use of the primary composition, or the oral composition or the cosmetic composition described above for the preparation of a product intended to protect the tissues of the skin against aging, in particular for inhibiting damage to the skin and/or mucous membranes by inhibiting collagenases and enhancing the synthesis of collagen. In fact, the use of the primary composition as described above, for example, makes it possible to enhance the bioavailability of the lycopene compound in the body and to slow down the aging of the skin. The primary compositions may also be useful in the prevention or treatment of sensible, dry or reactive skins, or for improving skin density or firmness, for ameliorating skin photoprotection, for preventing or treating cardiovascular diseases or disorders and cancers. They have also particular benefits on hair and coat of pet animals, such as an improved hair or coat density, fibre diameter, colour, oiliness, glossiness and a help to prevent hair or coat loss.

The positive effects of the primary composition of the present invention on the skin of humans or pets can be measured by using conventional methods such as, for example, minimal erythemal dose (MED), colorimetry, transepidermal water loss, DNA repair, measure of interleukins and proteoglycans production, or collagenase activity, barrier function or cell renewal or ultrasonic echography.

EXAMPLES

Example 1

Study of the Stability of Lycopene Isomers

The stability of lycopene isomers was evaluated both in an organic solvent and in a tomato extract.

Materials

Lycopene-rich tomato oleoresin has been obtained from Indena s.p.a. (Milan, Italy). Its total lycopene content amounted to 9.1%, of which the all-E and the 5-Z isomers represented 93.5% and 6.5%, respectively. Two isomerized oleoresins were prepared by heating a suspension of tomato oleoresin in ethyl acetate (1:10 w/w) either for 1 h or for 48 h. After cooling at room temperature, the suspensions were centrifuged and ethyl acetate in the recovered supernatants was removed by distillation under reduced pressure.

Di-t-butyl-hydroxy-toluene (BHT) and N-ethyldiisopropylamine were from Fluka AG. All solvents were HPLC grade and were used without purification.

Isolation of Pure Lycopene Isomers

Pure 5-Z, 9-Z, 13-Z and all-E lycopene were isolated from isomerised tomato oleoresin (submitted to 1 hour heating), by collecting the fractions containing the corresponding peaks after HPLC separation (see below the experimental conditions). Peaks were collected during two consecutive HPLC runs and the corresponding fractions were pooled.

Lycopene Analysis

Amount of total lycopene was determined by reverse phase HPLC on a $C_{18}$ precolumn (ODS Hypersil, 5 μm, 20×4 mm; Hewlett Packard, Geneva, Switzerland) and a $C_{18}$ column (Nova pak, 3.9 μm i.d.×300 mm length, Millipore, Volketswil, Switzerland). The separation was achieved at room temperature under isocratic conditions with a mobile phase consisting of acetonitrile/tetrahydrofuran/methanol/ammonium acetate 1% (533.5:193.6:53.7:28, wt/wt/wt/wt). The mobile phase flow rate was 1.5 mL/min.

Lycopene isomer profiles were determined by normal phase HPLC according to the method described by Schierle et al. (Schierle, J., Bretzel, W., Buhler, I., Faccin, N., Hess, D., Steiner, K., Schuep, W. (1997). Food. Chem. 59: 459). Samples of isomerized oleoresins were dissolved in n-hexane containing 50 ppm BHT and spun at maximum speed in an Eppendorf Lab centrifuge. The resulting supernatants were immediately analyzed by HPLC. The HPLC system used was a 1100 series Hewlett-Packard model equipped with an ultraviolet-visible photodiode array detector. Data were simultaneously acquired at 470 nm, 464 nm, 346 nm and 294 nm. Samples (10 μL) were separated using a combination of three Nucleosil 300-5 columns (4 mm internal diameter×250 mm length, Macherey-Nagel). The separation was achieved at room temperature under isocratic condition with a mobile phase consisting of n-hexane with 0.15% N-ethyldiisopropylamine. Flow rate was 0.8 mL/min. Lycopene Z-isomers were identified according to literature data.

Amounts of lycopene isomers were calculated based on surface areas of the HPLC peaks using the same extinction coefficient as the all-E lycopene. Therefore, the lycopene concentration in products containing Z-isomers is slightly underestimated since it is recognized that the extinction coefficients of Z-isomers are lower than that of the all-E isomer.

Conditions for Stability Tests

Stability of lycopene isomers was investigated both in n-hexane and in a tomato oleoresin isomerized by 4 hour heating in ethyl acetate. For this purpose, pure lycopene isomers were stored for 33 days in n-hexane at room temperature and in the absence of light, and the isomerized tomato oleoresin was kept for 55 days at room temperature in the absence of light. Total lycopene concentration and lycopene isomer profiles were measured at various time intervals during the storage.

Results

Stability of Lycopene Isomers in N-Hexane

Results of the stability test of pure lycopene isomers during storage in n-hexane at room temperature in the absence of light are reported Table 1. All isomers, i.e. included the all-E isomer, underwent a geometrical isomerization during storage. The 13-Z was the less stable isomer: whereas less than 50% of 5-Z, 9-Z and all-E lycopene were transformed after 33 day storage, more than 80% of 13-Z lycopene was converted into other isomers during this period of time. Also, the transformation pathway was different for the 13-Z lycopene compared to the other Z-isomers: while the 13-Z isomer was mainly converted into the all-E isomer, the 5-Z and 9-Z isomers were principally transformed into other Z-isomers during storage in n-hexane.

TABLE 1

Stability of pure lycopene isomers in n-hexane during storage at room temperature

|  | time (days) | concentration (% of total isomers) | | | |
| --- | --- | --- | --- | --- | --- |
|  |  | all E | 13-Z | 9-Z | 5-Z | x-Z |
| all-E lycopene | 0 | 97.6 | 1.4 | 0.5 | 0.5 | 0.1 |
|  | 1 | 86.0 | 10.1 | 1.2 | 1.2 | 1.5 |
|  | 2 | 78.4 | 15.0 | 1.1 | 2.6 | 3.0 |
|  | 5 | 69.3 | 19.6 | 2.2 | 3.8 | 5.1 |
|  | 12 | 67.8 | 18.2 | 2.0 | 6.4 | 5.6 |
|  | 33 | 58.7 | 15.7 | 3.8 | 13.4 | 8.4 |
| 5-Z lycopene | 0 | 1.1 | n.d. | n.d. | 95.5 | 3.4 |
|  | 1 | 2.2 | n.d. | n.d. | 84.3 | 13.5 |
|  | 2 | 2.4 | n.d. | n.d. | 76.9 | 20.6 |
|  | 5 | 3.9 | n.d. | n.d. | 68.4 | 27.7 |
|  | 12 | 5.6 | 1.7 | 0.7 | 65.3 | 26.7 |
|  | 33 | 10.7 | 2.8 | 2.3 | 53.5 | 30.7 |
| 9-Z lycopene | 0 | 4.4 | 0.6 | 93.3 | 1.8 | 0 |
|  | 1 | 5.8 | 2.3 | 87.1 | 2.1 | 2.8 |
|  | 2 | 6.0 | 3.1 | 83.5 | 11.6 | 5.9 |
|  | 5 | 5.6 | 5.2 | 79.2 | 1.5 | 8.6 |
|  | 12 | 7.0 | 8.2 | 66.5 | 2.3 | 15.9 |
|  | 33 | 9.8 | 10.5 | 56.0 | 4.1 | 19.7 |
| 13-Z lycopene | 0 | 2.4 | 96.6 | 0 | 0 | 1.0 |
|  | 1 | 42.6 | 57.0 | 0.4 | 0 | 0 |
|  | 2 | 59.8 | 38.7 | 0 | 0 | 1.5 |
|  | 5 | 68.9 | 23.4 | 1.5 | 1.9 | 4.3 |
|  | 12 | 65.5 | 20.8 | 2.6 | 5.3 | 5.8 |
|  | 33 | 57.0 | 16.9 | 4.2 | 11.7 | 10.2 |

Stability of Lycopene Isomers in Tomato Oleoresin

Results of the stability test of lycopene isomers in a tomato oleoresin heated for 48 hours in ethyl acetate are reported in Table 2.

TABLE 2

Stability of lycopene isomers in isomerized tomato oleoresin during storage at room temperature (n = 2).

| Storage time (days) | Total lycopene (mg/g) | 13-Z % | 9-Z % | all-E % | 5-Z % |
| --- | --- | --- | --- | --- | --- |
| 0 | 055.6 ± 3.0 | 17.4 ± 0.4 | 32.7 ± 0.7 | 18.7 ± 0.6 | 12.0 ± 0.4 |
| 3 | 56.6 ± 0.8 | 12.4 ± 0.1 | 31.4 ± 0.3 | 25.6 ± 0.5 | 13.0 ± 0.1 |
| 5 | 58.7 ± 0.4 | 9.5 ± 0.0 | 30.6 ± 0.5 | 30.6 ± 0.6 | 14.0 ± 0.4 |
| 7 | 59.2 ± 0.1 | 7.3 ± 0.2 | 30.9 ± 0.7 | 32.9 ± 0.3 | 14.4 ± 0.2 |

TABLE 2-continued

Stability of lycopene isomers in isomerized tomato oleoresin during storage at room temperature (n = 2).

| Storage time (days) | Total lycopene (mg/g) | 13-Z % | 9-Z % | all-E % | 5-Z % |
|---|---|---|---|---|---|
| 11 | 59.3 ± 0.8 | 5.2 ± 0.1 | 29.4 ± 0.0 | 36.5 ± 0.1 | 15.0 ± 0.1 |
| 17 | 60.1 ± 0.9 | 3.3 ± 0.4 | 29.0 ± 0.4 | 38.9 ± 0.4 | 15.4 ± 0.4 |
| 20 | 58.8 ± 0.9 | 2.9 ± 0.3 | 29.2 ± 0.4 | 39.9 ± 1.3 | 15.2 ± 0.6 |
| 34 | 51.3 ± 7.7 | 2.2 ± 0.1 | 30.0 ± 0.1 | 40.1 ± 0.7 | 14.1 ± 1.0 |
| 47 | 53.9 ± 1.2 | 1.9 ± 0.6 | 30.0 ± 0.3 | 41.4 ± 0.7 | 14.6 ± 1.3 |

Total lycopene content was stable during storage at room temperature. However, the lycopene isomer profile markedly changed with a decrease of 13-Z lycopene content and an increase of the all-E lycopene. The content of 9-Z and 5-Z lycopene remained stable during the storage period.

Conclusion

Both stability tests have shown that the 13-Z lycopene was much less stable than either the 5-Z, or the 9-Z, or the all-E isomers. Consequently, an isomerized tomato oleoresin with a low level of 13-Z lycopene should exhibit a good stability of its lycopene isomer profile.

Example 2

Isomerized Tomato Oleoresin with Increased Bioavailability

Objective:

The objective of the present work was to investigate the bioavailability of various Z-lycopene isomers in humans. To elucidate the bioavailability of specific Z-lycopene isomer in human, tomato oleoresins have been enriched in different Z-lycopene isomers reaching about 60% of the content of total lycopene i.e. one rich in 5-Z lycopene, another one rich in 13-Z lycopene and the last one rich in a mixture of 9-Z lycopene and 13-Z lycopene.

Material and Method

Subject

Thirty healthy men were enrolled in the study. The inclusion criteria were that the subjects should be nonvegetarians and nonsmokers and that they have no metabolic disorders such as diabete; hypertension; renal, hepatic, or pancreatic disease; or ulcers. Subjects were normolipidemic, i.e. they had a ratio of plasma cholesterol to HDL cholesterol <5.0 and plasma triacylglycerol (TAG) concentrations <1.5 mmol/L. Because of the large amount of blood that was drawn during the study, subjects were required to have a blood hemoglobin concentration >13 g/dL. Subjects were excluded from the study if they used cholesterol-altering medication or hypolidemic treatment or vitamin and mineral supplements from 3 months before the start of the study until the completion of the study or had had major gastrointestinal surgery; exercised intensively, such as running marathons; and consumed daily >2 glasses of wine (3 dL), >2 beers (3 dL), or >1 glass (shot glass) of hard liquor. Twenty-seven of the 30 volunteers completed the 4 post-prandial tests. Three volunteers abandoned the trial before the end for the following reasons: unavailability, medical treatment related to an eye injury, nausea related to the consumption of fatty meals. Subjects were 24±1 y old with a body weight of 70±1 kg and body mass index (BMI) of 22.5±0.3 kg/cm$^2$.

The protocol was approved by the ethical committee of Marseille (Marseille, France). Subjects received information on the background and design of the study and gave written informed consent before participation. They were free to withdraw from the study at any time.

Study Design

This was a double-blind, randomized, 4-periods, 4-treatments cross-over clinical trial with a washout period of 3 weeks minimum. After an overnight fast, subjects arrived at the Clinical Pharmacology and Therapeutic Trial Center of University of Marseille and consumed a standard meal consisting of 25 mg lycopene incorporated in 40 g peanut oil that was mixed with 70 g wheat semolina (cooked with 200 mL tap water). In addition, they consumed 40 g bread, 60 g cooked egg whites, a 125 g yoghurt containing 5 g of white sugar and drank 330 mL of water (Aquarel, Nestle). This standard meal provided 842 kcal (3520 kJ) with the following nutrient composition: protein (11.7%), carbohydrates (39.3%) and lipids (49.0%). This meal was consumed within 15 min. No other food was allowed over the subsequent 6 h, but subjects were allowed to drink up to a bottled water (330 ml) during the last 3 h post-absorption (Aquarel, Nestle).

Lycopene Supplements

Four different tomato products were tested providing each one 25 mg of total lycopene. They consisted of:

Tomato paste (Thorny, Switzerland) containing lycopene mostly in all-E configuration Tomato oleoresin enriched in 5-Z lycopene Tomato oleoresin enriched with 13-Z lycopene Tomato oleoresin enriched with a mixture of 9-Z and 13-Z lycopene Table 3 presents the lycopene content as well as the lycopene isomer profile of these four tomato products.

TABLE 3

Total lycopene as well as all-E and sum of Z-lycopene isomers in the four tomato products

| | All-E (% of total lycopene) | 5-Z (% of total lycopene) | 9-Z (% of total lycopene) | 13-Z (% of total lycopene) | X*-Z (% of total lycopene) |
|---|---|---|---|---|---|
| Tomato paste | 94.9 | 4.1 | nd | 0.1 | nd |
| 5-Z | 33.4 | 65.3 | 1.3 | nd | nd |
| 13-Z | 29.3 | 7.6 | 9.6 | 41.5 | 12.0 |
| 9- & 13-Z | 27.7 | 7.7 | 30.8 | 23.5 | 10.2 |

*unidentified lycopene isomers is a pool of unknown lycopene isomers calculated from the corresponding peak areas in the HPLC chromatogram.

Collection of Blood Samples

Fasting blood was drawn from an anticubital vein by venipuncture into an evacuated tube containing potassium EDTA/K$_3$ that was immediately placed in an ice-water bath and covered with an aluminium foil to avoid light exposure. Fasting blood samples were collected before i.e. 20 minutes and 5 minutes before consumption of the standard meal as well as 2 h, 3 h, 4 h, 5 h, 6 h post-absorption. The tube containing the blood was protected from light, stored at 4° C. and then centrifuged within 2 h (10 min, 4° C., 2.800 rpm) to separate the plasma. A cocktail of inhibitors (10 µL/mL) was added (Cardin et al., Degradation of apolipoprotein B-100 of human plasma low density lipoproteins by tissue and plasma kalikreins, Biol Chem 1984; 259:8522-8.).

Isolation of Plasma Triglyceride-Rich Lipoproteins (TRL)

After consumption of a fatty meal, dietary lipophilic molecules are incorporated into chylomicrons, which are secreted into blood. Lipoproteins are separated by ultracentrifugation methodology based on their density. Due to the quite similar density of chylomicrons (0.95 g/ml) and VLDL (1.006 g/ml), it is not possible to separate one from the other and they are collected altogether in a fraction called triglyceride-rich lipoproteins (TRL). However, in the post-prandial state, this plasma TRL fraction contains mainly chylomicrons secreted from the intestine, which is a good assessment of the intestinal bioavailability.

Triglyceride-rich lipoproteins (TRL) containing mainly chylomicrons with little amount of VLDL were immediately isolated by ultracentrifugation as follows: 6 mL of plasma were overlaid with a 0.9% NaCl solution and ultracentrifuged for 28 min at 32.000 rpm, at 10° C. in a SW41TI rotor (Beckman), in a L7 ultracentrifuge (Beckman). Immediately after centrifugation, the TRL were aliquoted and stored at −80° C. before analytical determinations. Lycopene analyses were performed within 10 days, and triacylglycerol analyses within 30 days.

Analytical Determination

Triglycerides were assayed by an enzymatic and colorimetric method using a commercial kit (Kit Bio-Merieux).

Total lycopene and lycopene isomer profiles were determined by reverse phase and normal phase HPLC method, respectively (M. Richelle, K. Bortlik, S. Liardet, C. Hager, P. Lambelet, L. A. Applegate, E. A. Offord, J. Nutr. (2002) 132, 404-408.). Total lycopene content was calculated as the sum of the 5-Z, 9-Z, 13-Z, x-Z and all-E-lycopene isomers. Lycopene isomer was quantified using the extinction coefficient of all-E lycopene since the exact value for all individual Z-lycopene is still unknown. Profile of lycopene isomers is determined by the ratio of individual lycopene isomer to total lycopene expressed in percentage.

Statistical Analysis

Lycopene bioavailability was assessed by measuring the area under the lycopene concentration in TRL-time curve (AUC). This area was calculated over the 0-6 hour period using the trapezoidal method (AUC(0-6 h)). Data are presented as mean±SEM. The baseline concentration was the average of the concentrations measured in the two plasma samples collected before consumption of the standard meal containing 25 mg lycopene from the tomato matrix. For each subject and each lycopene treatment, calculation of the AUC (0-6 h) was performed by subtracting the baseline concentration from the concentration value measured at each time point post-absorption. If this value was negative, it was considered as zero.

For each treatment, if the distribution of the $AUC_{(0-6h)}$ was normal (Skewness and Kurtosis tests) with or without logarithmic transformation, comparison was performed by using a linear mixed model with treatment as fixed effect and subject as random effect.

All statistical analyses were done with SAS software (version 8.2; SAS Institute, Cary, N.C.). The rejection level in statistical tests was equal to 5%.

Results

Lycopene Bioavailability

Because the four tomato treatments induced a variation of the extent in triglyceride secretion, lycopene bioavailability has been normalized using triglyceride absorption ($AUC_{(0-6h)}$).

Normalized lycopene bioavailability was markedly different between the four tomato treatments (FIGURE).

Surprisingly, lycopene was better bioavailable, by about two times, from tomato oleoresin rich in 5-Z lycopene than from the other three treatments, i.e tomato paste, tomato oleoresin rich in 13-Z lycopene as well as tomato oleoresin rich in a mixture of 13-Z and 9-Z lycopene ($p<0.0001$) (FIGURE).

While lycopene was similarly bioavailable from tomato paste as from the mixture of 13-Z and 9-Z tomato oleoresin.

Lycopene present in 13-Z tomato oleoresin exhibited a slight but significant lower bioavailability ($p<0.03$) compared to tomato paste.

Conclusion

These results indicate that the configuration of the lycopene molecule affects markedly the trafficking of lycopene within the gastrointestinal tract and in consequence the amount of lycopene that is absorbed. Lycopene bioavailability from tomato extract rich in 5-Z lycopene is about double than that from tomato paste. In contrast, lycopene present in tomato extract rich in a mixture of 9-Z and 13-Z lycopene is similarly bioavailable to that present in tomato paste while tomato oleoresin rich in 13-Z lycopene presents a slightly less bioavailable lycopene. Several authors have already pointed out that the presence of Z-lycopene in a tomato product is associated with an increase of lycopene bioavailability. This is the first study demonstrating that the enhancement of lycopene bioavailability is specifically related to lycopene configuration, i.e. 5-Z lycopene>9-Z lycopene>13-Z lycopene.

Example 3

Extraction and Isomerization in Ethyl Acetate 52 kg of fresh tomatoes containing 100 ppm of lycopene are chopped and homogenized. Part of the water is distilled off under reduced pressure to obtain 18 kg of tomato concentrate. This is extracted with 36 l of water saturated ethyl acetate; during extraction, the mixture is kept at room temperature shielded from light and under stirring for 2 hours. The extract is then separated from the tomato concentrate. The above described procedure is repeated twice on such tomato concentrate, totally using 108 l of solvent. The combined extracts are washed in a separatory funnel with 27 l of water. The aqueous phase is then discarded while the organic phase is concentrated under reduced pressure to obtain a suspension with 10% w/v dry residue; the dry residue has a total lycopene content of 9.1% w/w and a Z isomer content of 0.46% w/w. This mixture is refluxed (76° C.) under stirring for 7 days before being concentrated to dryness under reduced pressure.

46.8 g of final extract with a total lycopene content of 9% w/w and a Z isomer content of 5.59% w/w are obtained; in particular, the E isomer content is 3.41% w/w and the 13-Z isomer content is 0.16% w/w. The HPLC profile of the extract is reported in the FIGURE.

Example 4

Extraction and Isomerization in Hexane 10 kg of fresh tomatoes containing 140 ppm of lycopene are chopped and homogenized. Part of the water is distilled off under reduced pressure to obtain 2.5 kg of tomato concentrate, which is extracted with 12.5 l of hexane. During extraction, the mixture is kept at room temperature shielded from light and under stirring for 2 hours. The extract is then separated from the tomato concentrate. The above described procedure is repeated once on such tomato concentrate, totally using 25 l of solvent. The extracts are combined and concentrated under reduced pressure to obtain a solution with 10% w/v dry residue; the dry residue has a total lycopene content of 9.1% w/w and a Z isomer content of 0.46% w/w. This mixture is refluxed (69° C.) under stirring for 6 days before being concentrated to dryness under reduced pressure.

16.5 g of final extract with total lycopene content of 9.1% w/w and Z isomer content of 5.62% w/w are obtained; in particular, the E isomer content is 3.38% w/w and the 13-Z isomer content is 0.18% w/w.

Example 5

Isomerization in Butanol 10 kg of fresh tomatoes containing 90 ppm of lycopene are chopped and homogenized. Part of the water is distilled off under reduced pressure to obtain 3.4 kg of tomato concentrate, which is extracted with 7 l of water-saturated ethyl acetate. During extraction, the mixture is kept at room temperature shielded from light and under stirring for 2 hours. The extract is then separated from the tomato concentrate. The above described procedure is repeated twice on such tomato concentrate, totally using 21 l of solvent. The combined extracts are washed in a separatory funnel with 5.3 l of water. The aqueous phase is then discarded while the organic phase is concentrated to dryness under reduced pressure. The dry residue (9.8 g), which has a total lycopene content of 7.8% w/w and a Z-isomer content of 0.40% w/w, is suspended in 98 ml of n-butanol. The mixture is kept at 130° C. under stirring for 4 hours before being concentrated to dryness under reduced pressure. 9.8 g of final extract with a total lycopene content of 6.35% w/w and a Z-isomer content of 4.50% w/w are obtained; in particular, the E-isomer content is 1.85% w/w and the 13-Z isomer content is 0.47% w/w.

Example 6

Isomerization on Solid Catalysts

Materials

Lycopene-rich tomato oleoresin has been obtained from Indena s.p.a. (Milan, Italy). Its total lycopene content amounted to 9.1%, of which the all-E and the 5-Z isomers represented 93.5% and 6.5%, respectively.

Methods

A suspension of tomato oleoresin in acetyl acetate (1:100 w/w) was filtered and incubated with 5% of solid catalyst under constant stirring at room temperature for 2 h. The mixture was centrifuged at maximum speed in an Eppendorf Lab centrifuge and an aliquot of supernatant evaporated under $N_2$ and re-suspended in n-hexane/BHT.

Lycopene Analysis

Amount of total lycopene and lycopene isomer profiles were determined by reverse phase and normal phase HPLC, respectively, under the analytical conditions described in example 1.

Results

Lycopene isomer profiles measured in tomato oleoresin isomerised for 2 h at room temperature using solid catalysts are reported in Table 4.

TABLE 4

Lycopene isomer profiles in tomato oleoresins isomerised using solid catalysts

| Catalyst | Isomer concentration (% of total isomers) | | | | |
| --- | --- | --- | --- | --- | --- |
| | All-E | 13-Z | 9-Z | 5-Z | x-Z* |
| control | 83.3 | 3.0 | 0.9 | 8.6 | 4.1 |
| Tonsil Optimum | 31.3 | 7.0 | 13.4 | 23.8 | 24.5 |
| Amberlyst 15 | 34.5 | 4.8 | 11.2 | 19.4 | 30.1 |

*unknown lycopene isomers

Lycopene was efficiently isomerised during 2 h reaction in ethyl acetate at room temperature in the presence of either Tonsil Optimum or Amberlyst 15. With both catalysts a large fraction of lycopene all-E isomer was converted into Z-isomers. Among the identified lycopene isomers, the 5-Z was majoritairement formed, followed by the 9-Z and the 13-Z, respectively; thus, concentration of the 13-Z isomer was, thus, below 10% in the isomerised tomato oleoresins.

The invention claimed is:

1. A method of manufacturing a stable composition enriched in cis-lycopene (Z isomers) comprising:
    extracting lycopene from a lycopene-containing material by prolonged continuous heating in a solvent at a temperature of from 50° C. to 150° C. for a period of from 4 to 240 hours, and then removing the solvent therefrom to recover said stable composition enriched in cis-lycopene.

2. The method of claim 1 in which the lycopene-containing material consists of tomatoes, parts of tomatoes, derivatives thereof or tomato extracts in solvents.

3. The method of claim 1 wherein the solvent is a C3-C10 aliphatic hydrocarbon, a C1-C3 chlorinated solvent, a C3-C6 ester, a C3-C8 ketone or a C1-C8 alcohol.

4. The method of claim 3 wherein the solvent is selected from hexane, carbon tetrachloride, ethyl acetate, acetone, butanol.

* * * * *